(12) United States Patent
Oliphant et al.

(10) Patent No.: US 12,125,565 B2
(45) Date of Patent: Oct. 22, 2024

(54) PATIENT TEST DATA PROCESSING SYSTEM AND METHOD

(71) Applicant: Goodmark Medical (International) Limited, Edinburgh (GB)

(72) Inventors: Iain Oliphant, Edinburgh (GB); Liam John Scott Gove, Edinburgh (GB); Michael David Clark, Edinburgh (GB); Aleksandra Szymanczak, Edinburgh (GB); Neil Farish, Edinburgh (GB)

(73) Assignee: Goodmark Medical (International) Limited, Edinburgh (GB)

( * ) Notice: Subject to any disclaimer, the term of this patent is extended or adjusted under 35 U.S.C. 154(b) by 0 days.

(21) Appl. No.: 16/079,982

(22) PCT Filed: Feb. 9, 2017

(86) PCT No.: PCT/GB2017/050333
§ 371 (c)(1),
(2) Date: Aug. 24, 2018

(87) PCT Pub. No.: WO2017/144853
PCT Pub. Date: Aug. 31, 2017

(65) Prior Publication Data
US 2019/0066824 A1 Feb. 28, 2019

(30) Foreign Application Priority Data

Feb. 25, 2016 (GB) ..................... 1603309

(51) Int. Cl.
*G16H 10/60* (2018.01)
*G06F 9/54* (2006.01)
*G16H 10/20* (2018.01)

(52) U.S. Cl.
CPC ............. *G16H 10/60* (2018.01); *G06F 9/547* (2013.01); *G16H 10/20* (2018.01)

(58) Field of Classification Search
CPC ........ G16H 10/20; G16H 10/60; G16H 40/20; G16H 50/20; G06F 9/00; G06F 9/547;
(Continued)

(56) References Cited

U.S. PATENT DOCUMENTS 7,720,804 B2 5/2010 Fazal et al.
7,917,378 B2 3/2011 FitzGerald et al.
(Continued)

FOREIGN PATENT DOCUMENTS

WO WO-2013095459 A1 * 6/2013 ........... A61B 5/0024

OTHER PUBLICATIONS

Gaynor, Mark, et al. "A general framework for interoperability with applications to healthcare." Health Policy and Technology 3.1 (2014): 3-12. (Year: 2014).*
(Continued)

*Primary Examiner* — Mamon Obeid
*Assistant Examiner* — Chance L Smith
(74) *Attorney, Agent, or Firm* — Millen, White, Zelano & Branigan P.C.; William F. Nixon

(57) ABSTRACT

A method at a server system for processing patient test data to provide a more automated method of inputting point of care test data into an electronic health record avoiding user intervention. Point of care test data can be automatically completed and uploaded into an electronic health record. If a point of care test order is required in an electronic health record, it can automatically be created or identified for the uploading of point of care test data to the electronic health record for association with the automatically created or identified order.

16 Claims, 6 Drawing Sheets

(58) Field of Classification Search
CPC ......... G06F 19/30; G06F 19/32; G06F 19/34; G06F 19/36; G06Q 50/22; G06Q 50/24
See application file for complete search history.

(56) References Cited

U.S. PATENT DOCUMENTS

| | | | |
|---|---|---|---|
| 2001/0039502 A1* | 11/2001 | Case | G16H 40/67 705/2 |
| 2006/0178954 A1 | 8/2006 | Thukral et al. | |
| 2013/0018356 A1* | 1/2013 | Prince | G06Q 50/24 604/506 |
| 2013/0056535 A1* | 3/2013 | Rowlandson | G16H 40/63 235/380 |
| 2013/0124225 A1 | 5/2013 | Keen et al. | |
| 2013/0159019 A1 | 6/2013 | Reicher et al. | |
| 2014/0136234 A1 | 5/2014 | Weinstein | |
| 2015/0025913 A1 | 1/2015 | Friedlander et al. | |
| 2015/0051922 A1* | 2/2015 | Rentas | G16H 10/40 705/3 |
| 2016/0357915 A1* | 12/2016 | Morris | G16H 10/60 |
| 2017/0161435 A1* | 6/2017 | Orosco | G16H 10/60 |
| 2018/0075223 A1* | 3/2018 | Morcillo Montejo | G16H 50/20 |
| 2018/0277240 A1* | 9/2018 | Hall | G16H 10/40 |
| 2021/0202083 A1* | 7/2021 | Walker | A61B 5/7275 |

OTHER PUBLICATIONS

Kasthurirathne, Suranga N., et al. "Enabling better interoperability for healthcare: lessons in developing a standards based application programing interface for electronic medical record systems." Journal of medical systems 39 (2015): 1-8. (Year: 2015).*
International Search Report dated Jun. 12, 2017, issued in International patent application PCT/GB2017/050333 filed Feb. 9, 2017.
Written Opinion dated dated Jun. 12, 2017, issued in International patent application PCT/GB2017/050333 filed Feb. 9, 2017.
Singapore Patent Application No. 11201808362W; Written Opinion; dated Sep. 3, 2020; 4 pages.
Examination report for corresponding AU patent application 2017223070 dated Dec. 23, 2021 (pp. 1-8).

* cited by examiner

PATIENT TEST DATA PROCESSING SYSTEM AND METHOD

FIELD

The present invention generally relates to a data processing system and method for processing patient test data.

BACKGROUND

Point-of-care testing (POCT) is medical testing at or near the site of patient care. The driving notion behind POCT is to bring the test conveniently and immediately to the patient. This increases the likelihood that the patient, physician, and care team will receive the results quicker, which allows for immediate clinical management decisions to be made. POCT includes: blood glucose testing, blood gas and electrolytes analysis, rapid coagulation testing, rapid cardiac markers diagnostics, drugs of abuse screening, urine strips testing, pregnancy testing, faecal occult blood analysis, food pathogens screening, haemoglobin diagnostics, infectious disease testing and cholesterol screening.

POCT is often accomplished through the use of transportable, portable, and handheld instruments (e.g., blood glucose meter, nerve conduction study device) and test kits. Small bench analysers or fixed equipment can also be used when a handheld device is not available—the goal is to collect the specimen and obtain the results in a very short period of time at or near the location of the patient so that the treatment plan can be adjusted as necessary before the patient leaves. Cheaper, smaller, faster, and smarter POCT devices have increased the use of POCT approaches by making it cost-effective for many diseases, such as diabetes, carpal tunnel syndrome (CTS) and acute coronary syndrome.

There is a desire to get output of a POCT device made available immediately within an electronic medical record. The advantage of such integration into electronic medical health records is that results can be shared instantaneously with all members of the medical team through the software interface enhancing communication by decreasing turn-around time (TAT). Also, errors caused by manual input are avoided. One of the challenges accompanying the use of POCT is the plethora of devices and tests which brings with it a high degree of complexity in integrating the POCT devices due to the lack of any agreed standard for data output from such devices. To further complicate matters, there are a number of electronic health record providers, each with its own requirements and non-standard data format. There is a need to simplify the collection of POCT data and to simplify the process of importing the POCT data into electronic health records for patients.

SUMMARY

Aspects of the invention can provide a more automated method of inputting point of care test data into an electronic health record avoiding user intervention. In one aspect, point of care test data can be automatically completed and uploaded into an electronic health record. In one aspect, if a point of care test order is required in an electronic health record, it can automatically be created or identified for the uploading of point of care test data to the electronic health record for association with the automatically created or identified order.

One aspect provides a server system for processing patient test data from at least one point of care device, the server system comprising a test data interface for receiving point of care test data for a patient; an electronic health record provider interface for interfacing with at least one electronic heath record provider's computer, the at least one electronic health record provider's computer storing electronic health records for patients; program memory storing computer code; and a processor for reading and implementing the computer code in the program memory; wherein the program memory stores computer code for implementation by the processor to; control the test data interface to receive the point of care test data for the patient, identify additional required data missing from the point of care test data for the patient according to electronic health record provider requirements, control the electronic health record provider interface to retrieve electronic health record data for the patient from a said electronic health record provider's computer, and process the retrieved electronic health record data for the patient to add data to the point of care test data for the patient to try to form complete point of care test data for the patient.

This aspect can also provide a method at a server system for processing patient test data from at least one point of care device, the method comprising receiving point of care test data for a patient; identifying additional required data missing from the point of care test data for the patient according to electronic health record provider requirements; retrieving electronic health record data for the patient from an electronic health record provider's computer, the electronic health record provider's computer storing electronic health records for patients; and processing the retrieved electronic health record data for the patient to add data to the point of care test data for the patient to try to form complete point of care test data for the patient.

Another aspect provides a server system for processing patient test data from at least one point of care device, the server system comprising a point of care interface for receiving point of care test data for a patient; an electronic health record provider interface for interfacing with at least one electronic heath record provider's computer, the at least one electronic health record provider's computer storing electronic health records for patients; an order type memory storing data on parameters for types of orders for point of care tests ordered by physicians, wherein different electronic health providers can require different order types; program memory storing computer code; and a processor for reading and implementing the computer code in the program memory; wherein the program memory stores computer code for implementation by the processor to control the test data interface to receive the point of care test data for the patient, if the point of care test data does not include an order identifier identifying an order in an electronic health record for the patient for the point of care test for the patient according to electronic health record provider requirements, compare parameters of the point of care test data to parameters of the stored types of orders to identify an order type; and use the electronic health record provider's interface to create and add a point of care test order to the point of care test data and the electronic health record for the patient at a said electronic health record provider's computer.

This aspect can also provide a method at a server system for processing patient test data from at least one point of care device, the method comprising receiving point of care test data for a patient; if the point of care test data does not include an order identifier identifying an order in an electronic health record for the patient for the point of care test for the patient according to electronic health record provider requirements, compare parameters of the point of care test data to parameters of stored types of orders to identify an order type, wherein different electronic health providers can require different order types; and use an electronic health record provider's interface to create and add a point of care test order to the point of care test data and an electronic health record for the patient at an electronic health record provider's computer, the at least one electronic health record provider's computer storing electronic health records for patients.

A further aspect provides a server system for processing patient test data from at least one point of care device, the server system comprising a test data interface for receiving point of care test data for a patient; an electronic health record provider interface for interfacing with at least one electronic heath record provider's computer, wherein the at least one electronic health record provider's computer stores electronic health records for patients including point of care test data and uses notification and/or verification flags for workflow control for point of care test data in the electronic health record; program memory storing computer code; and a processor for reading and implementing the computer code in the program memory; wherein the program memory stores computer code for implementation by the processor to; control the test data interface to receive the point of care test data for the patient, and control the electronic health record provider interface to transmit the point of care test data for the patient to a said electronic health record provider's computer for inclusion in the electronic health record for the patient and to set the notification and/or verification flags for the point of care test data for the patient dependent upon parameters of the point of care test data for the patient.

This aspect can also provide a method at a server system for processing patient test data from at least one point of care device, the method comprising receiving point of care test data for a patient; and controlling an electronic health record provider interface to transmit the point of care test data for the patient to an electronic health record provider's computer for inclusion in an electronic health record for the patient and to set notification and/or verification flags for the point of care test data for the patient in the electronic health record for the patient at the electronic health record provider's computer dependent upon parameters of the point of care test data for the patient, wherein the electronic health record provider's computer uses the notification and/or verification flag for workflow control for the point of care test data in the electronic health record.

DETAILED DESCRIPTION

Figure 1:
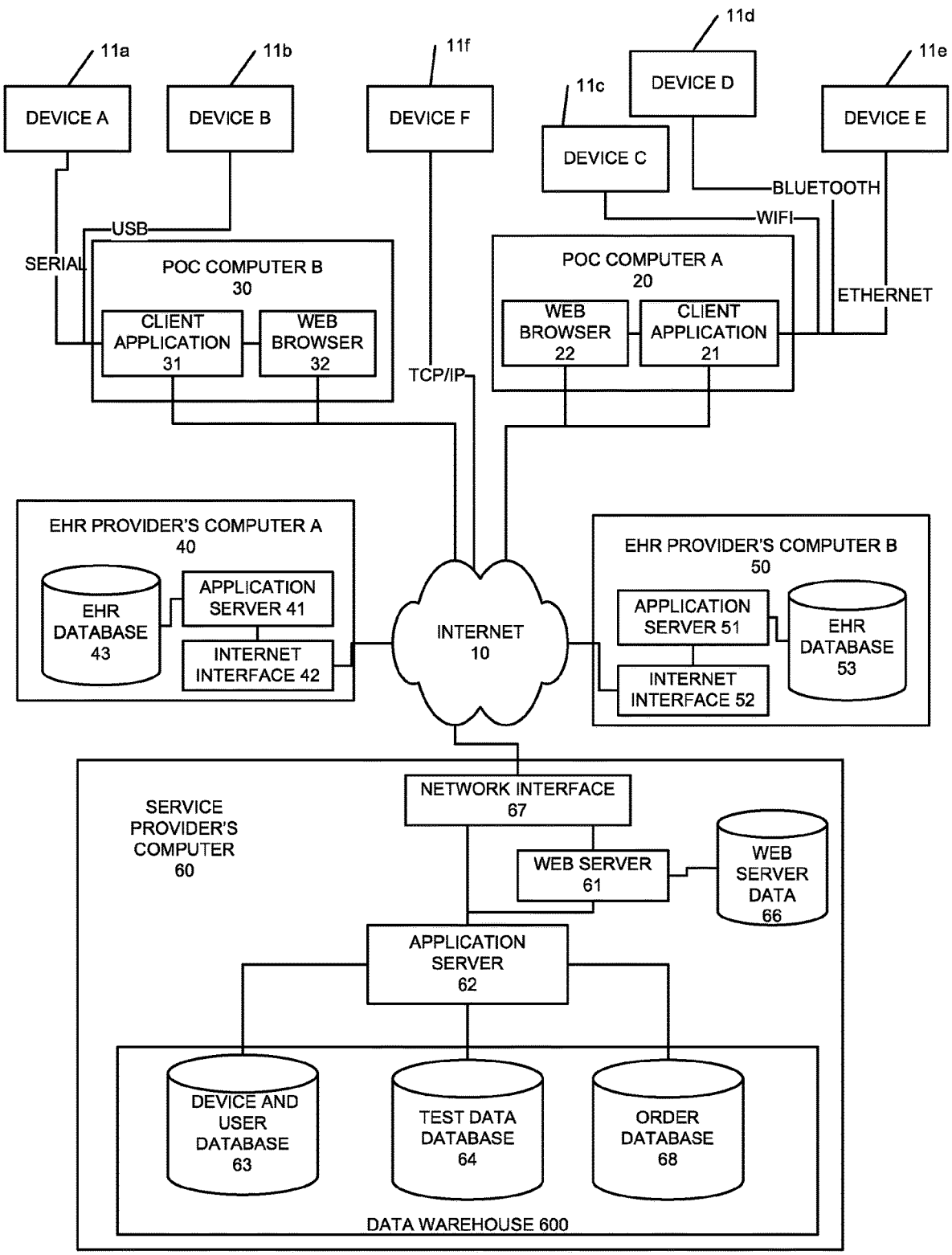
FIG. 1 is a schematic diagram of a system for processing patient test data according to one embodiment of the invention.

A first generalised embodiment comprises a server system for processing patient test data from at least one point of care device, the server system comprising a test data interface for receiving point of care test data for a patient; an electronic health record provider interface for interfacing with at least one electronic heath record provider's computer, the at least one electronic health record provider's computer storing electronic health records for patients; program memory storing computer code; and a processor for reading and implementing the computer code in the program memory; wherein the program memory stores computer code for implementation by the processor to; control the test data interface to receive the point of care test data for the patient, identify additional required data missing from the point of care test data for the patient according to electronic health record provider requirements, control the electronic health record provider interface to retrieve electronic health record data for the patient from a said electronic health record provider's computer, and process the retrieved electronic health record data for the patient to add data to the point of care test data for the patient to try to form complete point of care test data for the patient.

In one embodiment the additional required data comprises an order identifier entered in the electronic health record for the patient indicting that the point of care test for the patient was ordered by a physician, and the retrieved electronic health record data comprises an order identifier from the electronic health record data for the patient.

In one embodiment the additional required data includes additional data and the retrieved electronic health record data comprises an order identifier and associated order data from the electronic health record data for the patient.

In one embodiment the computer code is adapted to be implemented by the processor to control the electronic health record provider interface to transmit the complete point of care test data for the patient to the electronic health record provider's computer for inclusion in the electronic health record for the patient.

In one embodiment the electronic health record provider interface comprises at least one API for interfacing to the at least one electronic health record provider's computer.

In one embodiment the computer code is adapted to be implemented by the processor to control the electronic health record interface to obtain the electronic health record provider requirements.

In one embodiment the computer code is adapted to be implemented by the processor to store point of care test data that could not be completed and to generate a notification to a user to enable the user to enter data to form complete point of care test data for the patient.

One generalised embodiment provides a method at a server system for processing patient test data from at least one point of care device, the method comprising receiving point of care test data for a patient; identifying additional required data missing from the point of care test data for the patient according to electronic health record provider requirements; retrieving electronic health record data for the patient from an electronic health record provider's computer, the electronic health record provider's computer storing electronic health records for patients; and processing the retrieved electronic health record data for the patient to add data to the point of care test data for the patient to try to form complete point of care test data for the patient.

In one embodiment the additional required data comprises an order identifier entered in the electronic health record for the patient indicating that the point of care test for the patient was ordered by a physician, and the retrieved electronic health record data comprises an order identifier from the electronic health record data for the patient.

In one embodiment the additional required data includes additional data and the retrieved electronic health record data comprises an order identifier and associated order data from the electronic health record data for the patient.

In one embodiment the method includes transmitting the complete point of care test data to the electronic health record provider's computer for inclusion in the electronic health record for the patient.

In one embodiment the electronic health record provider's computer is interfaced to the server system using an API.

In one embodiment the computer code is adapted to be implemented by the processor to control the electronic health record interface to obtain the electronic health recorder provider requirements.

In one embodiment the method includes storing point of care test data that could not be completed and generating a notification to a user to enable the user to enter data to form complete point of care test data for the patient.

One generalised embodiment provides a server system for processing patient test data from at least one point of care device, the server system comprising a point of care interface for receiving point of care test data for a patient; an electronic health record provider interface for interfacing with at least one electronic heath record provider's computer, the at least one electronic health record provider's computer storing electronic health records for patients; an order type memory storing data on parameters for types of orders for point of care tests ordered by physicians, wherein different electronic health providers can require different order types; program memory storing computer code; and a processor for reading and implementing the computer code in the program memory; wherein the program memory stores computer code for implementation by the processor to control the test data interface to receive the point of care test data for the patient, if the point of care test data does not include an order identifier identifying an order in an electronic health record for the patient for the point of care test for the patient according to electronic health record provider requirements, compare parameters of the point of care test data to parameters of the stored types of orders to identify an order type; and use the electronic health record provider's interface to create and add a point of care test order to the point of care test data and the electronic health record for the patient at a said electronic health record provider's computer.

In one embodiment the computer code is adapted to be implemented by the processor to control the electronic health record provider interface to create a point of care test order in the electronic health record data for the patient at the electronic health record provider's computer and to receive an order identifier for the created point of care test order from the electronic health record provider's computer, and add the received order identifier to the point of care test data.

In one embodiment the computer code is adapted to be implemented by the processor to control the electronic health record provider interface to transmit the point of care test data to the electronic health record provider's computer for inclusion in the electronic health record for the patient.

One generalised embodiment provides a method at a server system for processing patient test data from at least one point of care device, the method comprising receiving point of care test data for a patient; if the point of care test data does not include an order identifier identifying an order in an electronic health record for the patient for the point of care test for the patient according to electronic health record provider requirements, compare parameters of the point of care test data to parameters of stored types of orders to identify an order type, wherein different electronic health providers can require different order types; and use an electronic health record provider's interface to create and add a point of care test order to the point of care test data and an electronic health record for the patient at an electronic health record provider's computer, the at least one electronic health record provider's computer storing electronic health records for patients.

In one embodiment the electronic health record provider interface is controlled to create a point of care test order in the electronic health record data for the patient at the electronic health record provider's computer and to receive an order identifier for the created point of care test order from the electronic health record provider's computer, and the received order identifier is added to the point of care test data.

In one embodiment the point of care test data is transmitted to the electronic health record provider's computer for inclusion in the electronic health record for the patient.

One generalised embodiment provides a server system for processing patient test data from at least one point of care device, the server system comprising a test data interface for receiving point of care test data for a patient; an electronic health record provider interface for interfacing with at least one electronic heath record provider's computer, wherein the at least one electronic health record provider's computer stores electronic health records for patients including point of care test data and uses notification and/or verification flags for workflow control for point of care test data in the electronic health record; program memory storing computer code; and a processor for reading and implementing the computer code in the program memory; wherein the program memory stores computer code for implementation by the processor to; control the test data interface to receive the point of care test data for the patient, and control the electronic health record provider interface to transmit the point of care test data for the patient to a said electronic health record provider's computer for inclusion in the electronic health record for the patient and to set the notification and/or verification flags for the point of care test data for the patient dependent upon parameters of the point of care test data for the patient.

In one embodiment the electronic health record provider interface comprises at least one API for interfacing to the at least one electronic health record provider's computer.

One generalised embodiment provides a method at a server system for processing patient test data from at least one point of care device, the method comprising receiving point of care test data for a patient; and controlling an electronic health record provider interface to transmit the point of care test data for the patient to an electronic health record provider's computer for inclusion in an electronic health record for the patient and to set notification and/or verification flags for the point of care test data for the patient in the electronic health record for the patient at the electronic health record provider's computer dependent upon parameters of the point of care test data for the patient, wherein the electronic health record provider's computer uses the notification and/or verification flag for workflow control for the point of care test data in the electronic health record.

In one embodiment the electronic health record provider interface comprises an API for interfacing to the electronic health record provider's computer.

In one embodiment a non-transient storage medium stores computer readable code for controlling a computer to carry out any of the methods as described above.

In one embodiment a carrier medium carries computer readable code for controlling a computer to carry out any of the methods as described above.

In the following detailed description, reference is made to the accompanying drawings that form a part hereof, and in which is shown by way of illustration specific embodiments in which the inventive subject matter may be practiced. These embodiments are described in sufficient detail to enable those skilled in the art to practice them, and it is to be understood that other embodiments may be utilized and that structural, logical, and electrical changes may be made without departing from the scope of the inventive subject matter. Such embodiments of the inventive subject matter may be referred to, individually and/or collectively, herein by the term "invention" merely for convenience and without intending to voluntarily limit the scope of this application to any single invention or inventive concept if more than one is in fact disclosed.

The following description is, therefore, not to be taken in a limited sense, and the scope of the inventive subject matter is defined by the appended claims.

The functions or algorithms described herein are implemented in hardware, software or a combination of software and hardware in one embodiment. The software comprises computer executable instructions stored on computer readable media such as memory or other type of storage devices, or any other form of media such as a signal. Further, described functions may correspond to modules, which may be software, hardware, firmware, or any combination thereof. Multiple functions are performed in one or more modules as desired, and the embodiments described are merely examples. The software is executed on a digital signal processor, ASIC, microprocessor, or other type of processor operating on a system, such as a personal computer, server, a mobile device, or other device capable of processing data including network interconnection devices. The network can comprise a wired or wireless network and includes a private network, a virtual private network (VPN), a Local Area Network (LAN), a Wide Area Network (WAN) and the internet for example. Although in the following detailed embodiment the interconnection between computers is shown over the internet, the invention encompasses any form of network connection.

Some embodiments implement the functions in two or more specific interconnected hardware or software modules or devices with related control and data signals communicated between and through the modules, or as portions of an application-specific integrated circuit. Thus, the exemplary process flow is applicable to software, firmware, and hardware implementations.

Embodiments of the present invention can be implemented on any form of computing hardware using one or more computer programs or applications (software). The computer program(s) can be provided to a computer on any suitable carrier medium. One such type of medium is a computer storage medium which represents a non-transient medium. Computer storage media include random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Another form of medium is a transient medium such as a signal. A signal can comprise an electrical signal over a wire, an electromagnetic signal transmitted over a wire or wirelessly, an optical signal, an acoustic signal, or even a magnetic signal. Once common form of signal is transmitted over a communication network which can be wired or wireless or a combination of both, e.g. a local area network (LAN), a wide area network (WAN) or the internet.

The point of care devices can comprise any device for carrying out any patient medical test at a point of care facility or even at the patients premises, such as blood glucose testing, blood gas and electrolytes analysis, rapid coagulation testing, rapid cardiac markers diagnostics, drugs of abuse screening, urine strips testing, pregnancy testing, faecal occult blood analysis, food pathogens screening, haemoglobin diagnostics, infectious disease testing and cholesterol screening. A point of care facility can comprise any medical facility capable of providing such patient tests such as a doctor's surgery, a clinic, or a specialist centre. Where a point of care device is used by a patient in their own facilities either by themselves or by a visiting medical practitioner, the patient test data can be obtained as an output from the device on a storage media for later upload to a point of care computer, or as a signal to be transmitted over a communications network (wired or wireless) to the point of care computer.

A first embodiment of the present invention will now be described with reference to FIG. 1.

FIG. 1 schematically illustrates a patient test data gathering and processing system. Point of care devices 11a to 11f are provided to obtain patient test data. The point of care devices 11a to 11f are connected to interfaces in respective point of care (POC) computers 20 and 30. The POC computers 20 and 30 are provided at POC facilities or accessible to POC facilities. The POC devices 11a to 11f may be present at the POC facility or used at a remote location when portable e.g. at the patients premises or in a mobile facility. The POC devices 11a to 11f generate output patient test data as a result of a test being performed by an operator for a patient. The patient test data can be output using any known convenient method which depends upon the output capabilities of the POC device and includes:

From POC device A (11a) over a serial computer line to a serial computer port in the POC computer 30.

From POC device B (11b) over a USB link to a USB computer port in the POC computer 30.

From POC device C (11c) over a wireless Wi-Fi link to a wireless port in the POC computer 20.

From POC device D (11d) over a Bluetooth® link to a Bluetooth® port in the POC computer 20.

From POC device E (11e) over an Ethernet line to an Ethernet port in the POC computer 20.

From POC device F (11f) over an internet connection to an internet network interface so as to be able to upload the POCT data directly to the service provider's computer 60.

From a POC device the patient test data can also be stored onto a storage device such as a solid state memory device, an optical disk or even a magnetic disk to be read by an appropriate storage device reader in the POC computer or any other computer for the uploading of the POCT data to the service provider's computer 60.

In one embodiment, the POC devices are connected to the POC computer 20 and 30 via a local area network at a facility. The local area network can be a network provided at the facility for general networking of computers at the facility and hence the system can utilise the network already provided at the facility to connect POC devices located around a facility to the POC computer 20 and 30. If a POC device does not have a local area network interface, a network device can be provided connected to the output of the POC device to convert the output for output of the local area network. For example, such a network device can convert a USB output to a local area network output, or a serial output to a local area network output.

The POC computer 20 and 30 comprises any suitable computing device such as a general purpose computer, a server, a mobile device, a laptop, tablet computer etc. The POC computer 20 and 30 implements computer code in the form of a client application 21 and 31 and optionally a web browser application 22 and 32 can be included. The POC computer 20 and 30 has a connection via a network interface to the internet 10 over a wired or wireless network to provide the web browser application 22 and 32 and the client application 21 and 31 with access to send and receive data over the internet 10. A medical facility can include a single POC computer or multiple POC computers. The medical care provider operating the facility may operate more than one facility.

Although in this embodiment, the POC computer 20 and 30 can optionally include a web browser to provide a user interface to the service provider's computer 60, a user can use a web browser on any computer to access the web server 61 of the service provider's computer 60.

Electronic health records (EHR) are stored and can be maintained by EHR providers or by medical care providers. There are a number of such providers available and different medical care providers use different EHR providers. Usually a medical care provider uses a single EHR provider. The EHR providers host the EHR records in databases 43 and 53 on computers 40 and 50. In this embodiment, each EHR provider's computer 40 and 50 implements an internet interface 42 and 52 for interfacing via a network interface to the internet 10 and an application server 41 and 51 for providing the required functionality and interface to the respective EHR databases 43 and 53. To facilitate connection by the service provider's computer 60 to the application server 41 and 51, the internet interface 42 and 52 can comprise an application programming interface (API). The EHR provider's computers can in alternative embodiments be connected by any form of network connection over a network to enable the service provider's computer 60 to connect to it.

In this embodiment, the patient test data processing is hosted in a service provider's computer 60 comprising a server system implementing a Software as a Service (Saas) model, where a 'thin client' in the form of the client application 21 and 31 is implemented on each POC computer 20 and 30. On the service provider's computer 60 web services are implemented to provide the functionality. In this embodiment, on the POC computer 20 and 30 a Windows® service can be implemented to provide the functionality. In alternative embodiment, alternative well know implementations can be used.

As shown in FIG. 1 schematically, a web server 61 is provided with access to web server data 66 to provide a web interface for users. This enables an operator to login into the service and interact with interfaces generated by the web server 61 e.g. to view lists of and select cached patient test data, to input required additional patient test data, user preference parameters (such as manual or automatic processing of the patient test data for entry in an EHR of a patient) and EHR order data, etc. An application server 62 is provided to provide the functionality and access the device and user database 63, the test data database 64, and the order database 68 forming part of the data warehouse 600. Both the application server 62 and the web server 61 are connected by a network interface 67 to the internet 10. The device and user database 63 stores a library of test type objects defining a common data format for a type of test and hence forms a library store.

Figure 2:
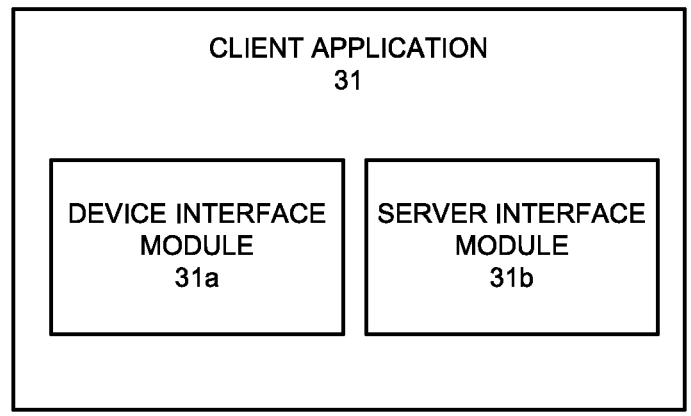
FIG. 2 is a schematic diagram of a client application according to one embodiment of the present invention.

FIG. 2 is a schematic diagram of a client application 31 according to one embodiment. The client application 31 comprises two distinct functional modules, namely a device interface module 31*a* for sending and receiving data to and from POC devices 11*a* to 11*f*, and a server interface module 31*b* for interfacing with the service provider's computer 60.

The web browser 32 illustrated in the POC device in FIG. 1 can provide a web interface to enable an operator to login to the service provider's computer 60, to view a list of and select cached patient test data, to enter required additional patient test data, to enter and view operator qualification data for regulatory compliance etc. Alternatively an operator can use any computer with a web browser to login and access the cached test data stored at the service provider's computer 60.

Figure 3:
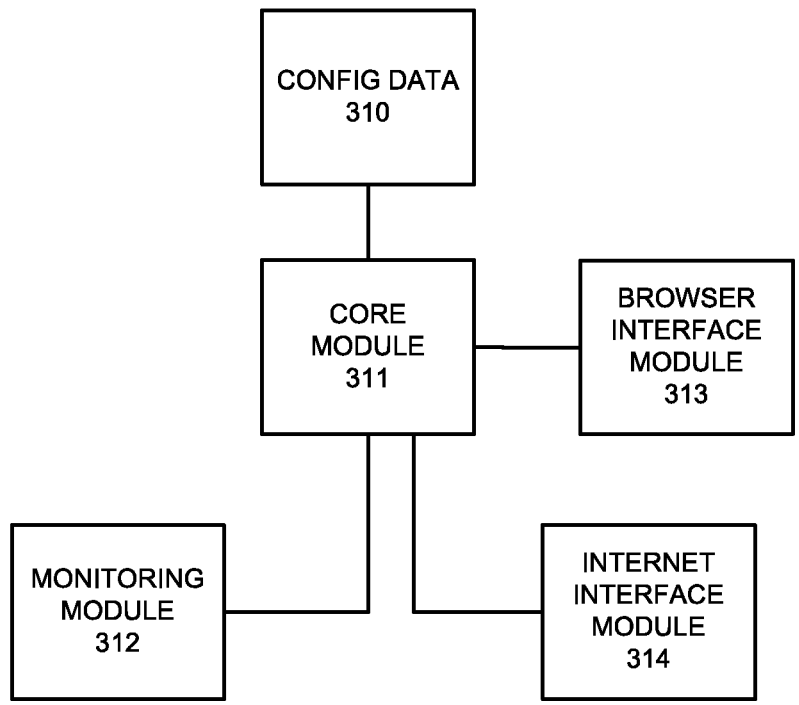
FIG. 3 is a schematic diagram of a client application according to one embodiment of the present invention.

FIG. 3 is a different schematic diagram of a client application 31 according to an embodiment of the invention. This schematic diagram illustrates that the client application 31 is composed of functional modules comprising configuration data 310 stored in non-volatile memory in the POC computer 30 storing configuration parameters for each POC device 11*a* to 11*f* connected to the POC computer 30. The configuration parameters can be entered by an operator, automatically detected, or downloaded from the service provider's computer 60. The configuration parameters include a device identifier and name, a connection type e.g. USB, Wi-Fi, serial, Ethernet, or Bluetooth, connection parameters e.g. port number, baud rate, parity etc. In addition to the POC device name, each POC device is assigned a unique identifier since a POC computer may be connected with more than one POC device with the same name e.g. ABC Inc Blood Tester. This use of stored configuration parameters that can be downloaded from the service provider's computer 60 from the device and user database 63 avoids the need for the operator to have to input the configuration parameters and instead relies on having a library of configuration parameters for POC devices stored in the service provider's computer 60. When a POC device is connected for the first time, the client application can carry out an auto detection routine to detect configuration data parameters for the selected POC devices. Such parameters include a device name, a connection type e.g. USB, Wi-Fi, serial, Ethernet, or Bluetooth, connection parameters e.g. port number, baud rate, parity etc. In addition to the POC device name, each POC device is assigned a unique identifier since a POC computer 20 or 30 may be connected with more than one POC device with the same name e.g. ABC Inc Blood Tester. Alternatively, the device name can be required to be the unique identifier. This process avoids the need for any input by the operator or the need for a library of configuration data for the POC devices, but it does require an algorithm for detecting the connection of POC devices and then for determining the configuration data.

In on embodiment a monitoring module 312 can be used to monitor the network and input ports of the POC computer 30 for data output to the POC computer 30 by the POC device 11*a* to 11*f*. A core module 311 controls the monitoring module 312 in according with the configuration parameters and receives the input patient test data and adds the POC device identifier and POC computer identifier to it before passing it to an internet interface module 314 to transmission to the service provider's computer 60. A browser interface module 313 is provided and controlled by the core module 311 to interface to the web browser 32 to enable an operator to login to the service provider's computer 60 to view a list of and select cached patient test data, to enter required additional patient test data, to enter and view operator qualification data for regulatory compliance etc.

Figure 4:
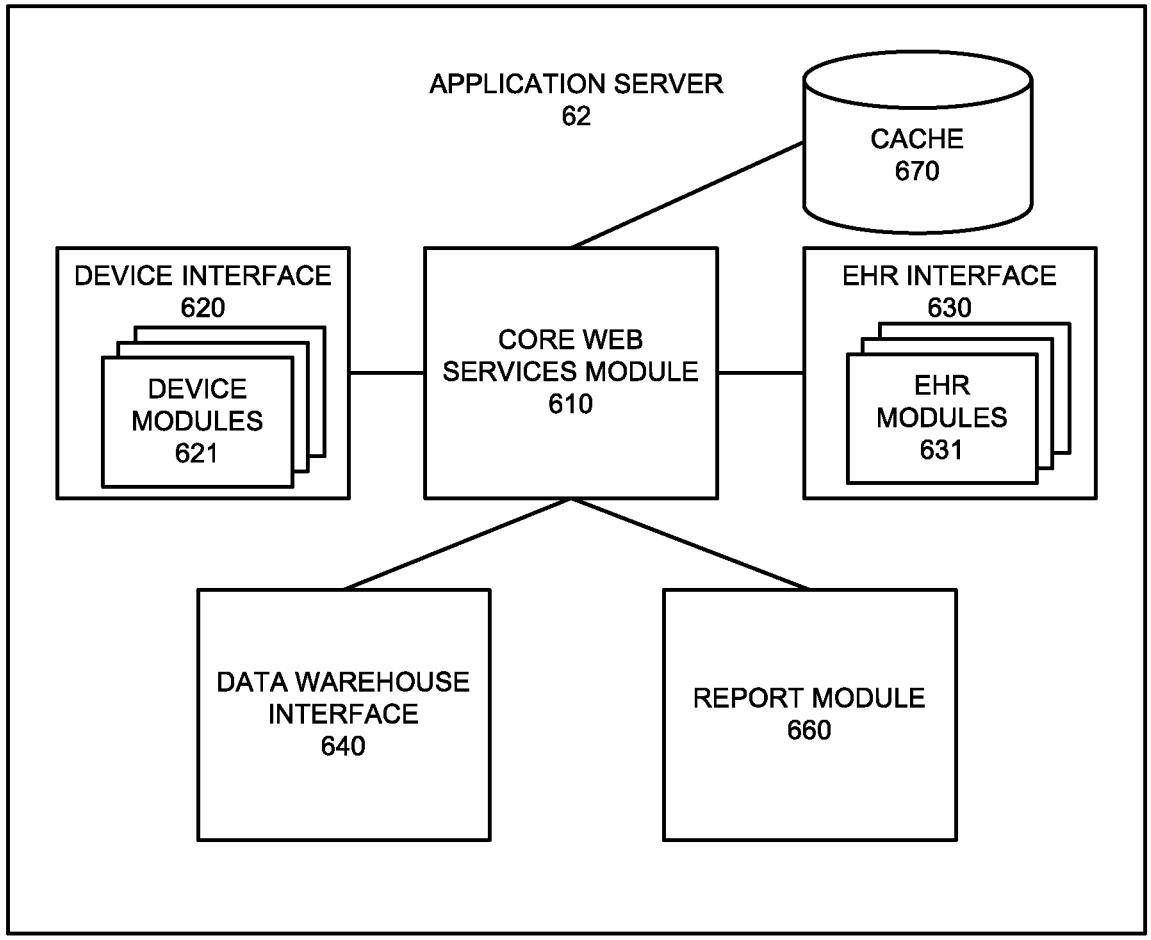
FIG. 4 is a schematic diagram of an application server according to one embodiment of the invention.

FIG. 4 is a schematic diagram of an application server 62 hosted on the service provider's computer system according to one embodiment. The application server 62 operates a core web services module 610 which has access to a cache memory 670 for temporary storage of patient test data pending approval and/or completion, and which provides an interface 640 to the data warehouse 600. A reports module 660 is provided to provide users of the service with access to reports on patient tests. A device interface module 620 is provided which implements specific device modules 621 dependent upon the identity of the devices detected in the patient test data. The device modules 621 receive the patient test data and perform device specific processing on it, namely the data which is in a format specific to the device is parsed using a parser specific to the device to reformat the data according to a test type object dependent upon the test type identified for the patient test data or using an knowledge of the format of the patient test data to apply appropriate parsing rules. The library of test type objects in the data warehouse 600 is accessed to identify the test type. The patient test data reformatted according to the identified test type can then be stored in the cache 670 pending approval and/or completion. An EHR interface 630 is also provided and implements EHR modules 631 which can be specific to the EHR provider to which the patient test data is to be transmitted. The EHR modules 631 can use a specific Application Programming Interface (API) made available by the EHR provider to enable data to be exchanged between the EHR provider's computer 40 and 50 and the service provider's computer 60. Alternatively, the data can formatted according to an agreed standard for EHR providers so that it can be recognised when uploaded to the EHR provider. The EHR provider can be identified from an order identifier associated with the patient's point of care test. When a medical practitioner places an order for a POCT in an EHR, the order is assigned a unique identifier and it is associated with the patient record and patient identifier in the EHR. As will be described in more detail herein after, when a patient test is performed an operator can input a patient name or identifier enabling the order to be found in the EHR and hence associated with the patient test data in the cache 670 of the service provider's computer 60 pending completion and acceptance of the patient test data by the operator if the operator has set the processing of the test data to require manual input or if the data is incomplete and cannot be automatically processed.

Figure 5:
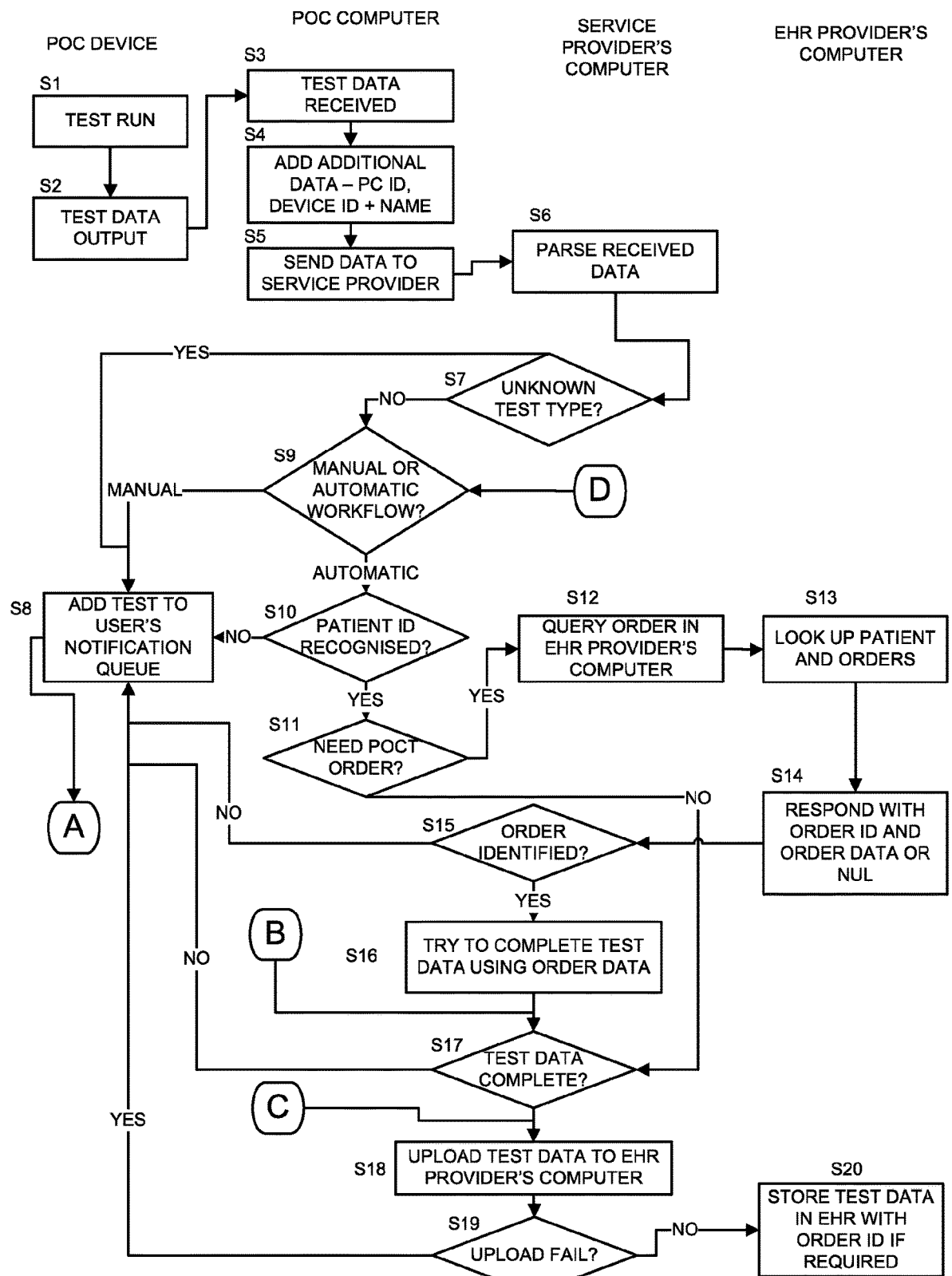
FIG. 5 is a flow diagram illustrating a method of processing patient test data according to one embodiment of the invention.

A method of operating the patient test processing system according to one embodiment will now be described with reference to FIG. 5. The steps of the following flow diagram performed by the service provider's computer are implemented by code executed by the service provider's computer 60.

A point of care test is performed on a patient in step S1 and the POC device outputs the point of care test data for the patient (step S2). The point of care test data is received by the POC computer 20 via a POC interface such as a serial interface, a USB interface, an Ethernet interface, a Wi-Fi interface or a Bluetooth® interface and 30 (step S3) and the client application 21 and 31 adds an identifier for the device POC computer 20 and 30, and a unique identifier and name for the POC device to the point of care test data (step S4). The point of care test data is then transmitted over a network interface to the service provider's computer 60 (step S5). Upon receipt at the service provider's computer 60 the device name is used to identify the device module 621 to implemented to process the patient test data from the POC device. The device module 621 verifies that the data is of the format that was expected for the POC device, parses the patient test data and stores the parsed point of care test data in the cache 670 (step S6). The parsing performed by the device modules 621 takes the point of care test data from the POC device and formats the point of care test data according to a test type determined from a test type library on the basis of the POC device in use. In other words, each device module 621 has an associated set of device test types that it can produce point of care tests for. Each device type is associated with the set of test types available to be run on that device. A user of the system can define a subset of test types they wish to use for each device based upon the specific consumables they use with the device.

The point of care test data for a patient is then assigned a unique test identifier and processed to determine whether the parameters are in a form of a known test type. If they are not (step S7) the test data is stored in the cache 670 and not processed further and information on the test is added to a queue for the user (e.g. operator of the POC computer) in step S8. The user or operator is indirectly identified in the point of care test data by the inclusion of an identifier for the facility at which the POCT was performed. The users are associated with the facility in the database. This allows the operator to login to the service provider's computer 60, as a user associated with the identified facility, to view and correct, update or complete point of care test data for patients that had POC test performed at their facility, as will be described in more detail herein after.

If the test type is recognised as known in step S7, in step S9, it is determined whether the operator has set a flag in the system that determines whether the point of care test data is to be processed automatically or manually. A flag can be set for all POC test performed at a facility point of care test data or just for certain types of test data or even for certain patients. If the flag is set for the point of care test data to manual, the test data is stored in the cache 670 and not processed further and information on the test is added to a queue for the user (e.g. operator of the POC computer) in step S8.

If the point of care test data is to be automatically processed, in step S10 the process determined whether the patient identifier included in the point of care test data is recognised. The patient identifier may be a Medical Record Number (MRN).

Alternatively, if the point of care data includes the patient's full name and date of birth, this can be recognised as the patient's identifier. The facility identifier included in the POCT data can also be used to assist in the identification of the patient by reference to the EHR provider's computer if the patient identifier information in the POCT data is not sufficient to uniquely identify the patient. It is possible for EHR data to be queries using the EHR interface using the POCT data to try to uniquely identify the patient. For example, the facility identifier, the limited patient information (such as first and last name) and the POC test type can enable an order for the test to be identified in the EHR records and hence the identity of the patient can be ascertained i.e. an MRN determined and added to the POCT data.

If the patient's identifier is not recognised, the test data is stored in the cache 670 and not processed further and information on the test is added to a queue for the user (e.g. operator of the POC computer) in step S8. If the patient identifier is recognised, the process then determines in step S11, based on which electronic health provider is to be used, whether an order for the point of care test is required in an electronic health record for the patient. The determination of which electronic health record provider is to be used can be based on an agreement with the provider, or data in the point of care test data such as part of data associated with a point of care test order. Normally a health care provider operating a facility will select an EHR provider and this association between a facility (as identified in the POCT data) and the EHR provider can be used to identify the EHR provider. In an alternative embodiment, if there is no indication of an electronic health record provider to be used and one cannot be determined from the POCT data, the system can select a first one to try and can repeat the process for a number of electronic health record providers.

If a point of care test order is required for the electronic health record provider, in step S12 a query is sent to the electronic health record provider's computer with the patient identifier to identify the patient's electronic health record. In step S13 the electronic health record provider's computer looks up the patient's electronic health record and identifies any outstanding point of care test orders in their electronic health record. An outstanding point of care test order can be flagged as unfulfilled in the electronic health record. This flag can be set to fulfilled when the point of care test data is uploaded, either automatically by the EHR or by an additional instruction over the EHR interface. If there is more than one order outstanding for a patient, the most suitable order can be determined based on a best match to the POCT data and the order type information for the facility. In step S14, the electronic health record provider's computer responds to the query with an order identifier and order data or a null indicating than no order was found. The order data returned to the service provider's computer 60 can comprise not just data specific to the order but also selected data from the electronic health record. The data can comprise any data that may be useful for addition to the point of care test data to complete the set of data to meet the requirements set by the electronic health provider. Electronic health providers can define the data and the data format required for point of care test data to be able to be uploadable to the electronic health record.

If the electronic health record provider's computer returns a null indicating that there was no point of care test order identified, in step S15, the test data is stored in the cache 670 and not processed further and information on the test is added to a queue for the user (e.g. operator of the POC computer) in step S8. If the electronic health record provider's computer returns an order identifier, in step S15 the process moves on to step S16 where the returned order data is used to try to complete any missing data for the point of care test data. The missing data can be identified as data missing compared with the data set required by the electronic health record provider before a point of care test can be uploaded into an electronic health record.

The process then determines whether the point of care test data is complete i.e. matches the requirement of the electronic health record provider in step S17. If not, the system has been unable to automatically complete the data set and manual intervention is required. Hence, the test data is stored in the cache 670 and not processed further and information on the test is added to a queue for the user (e.g. operator of the POC computer) in step S8. If the test data is complete, in step S18 the point of care test data is uploaded to the electronic health provider's computer. In step S19, the upload process is monitored to determine if it fails. If it does fail, the test data is stored in the cache 670 and not processed further and information on the test is added to a queue for the user (e.g. operator of the POC computer) in step S8. If the upload is successful, in step S20 the point of care test data is stored in the electronic health record with the order identifier by the electronic health record provider's computer.

If in step S11 it is determined that the electronic health record provider does not require an order for the point of care test in the electronic health record for the patient, the process jumps to step S17 to determine if the point of care test data is complete i.e. matches the requirement of the electronic health record provider in step S17. If not, the system has been unable to automatically complete the data set and manual intervention is required. Hence, the test data is stored in the cache 670 and not processed further and information on the test is added to a queue for the user (e.g. operator of the POC computer) in step S8. If the test data is complete, in step S18 the point of care test data is uploaded to the electronic health provider's computer. In step S19, the upload process is monitored to determine if it fails. If it does fail, the test data is stored in the cache 670 and not processed further and information on the test is added to a queue for the user (e.g. operator of the POC computer) in step S8. If the upload is successful, in step S20 the point of care test data is stored in the electronic health record by the electronic health record provider's computer.

As can be seen from the description of the operation of the embodiments, the use of the cache for storing the point of care test data at the service provider's computer 60 ensures that the patient test data is stored and available for uploading to the EHR provider's computers 40 and 50 and can wait if an EHR provider's computer 40 and 50 becomes unavailable until it becomes available so no patient test data is lost. The point of care test data is only stored in the test data database 64 of the data warehouse 600 when the point of care test data is uploaded to an electronic health record provider's computer. Thus a record of the uploaded point of care test data is kept which is separate to the electronic health record providers.

In the process described with reference to FIG. 1, if the electronic health record provider requires an order for a point of care test before it can be uploaded into the electronic heath record and one is not provided in the point of care test data, the process is unable to proceed further automatically and requires manual intervention.

Figure 6:
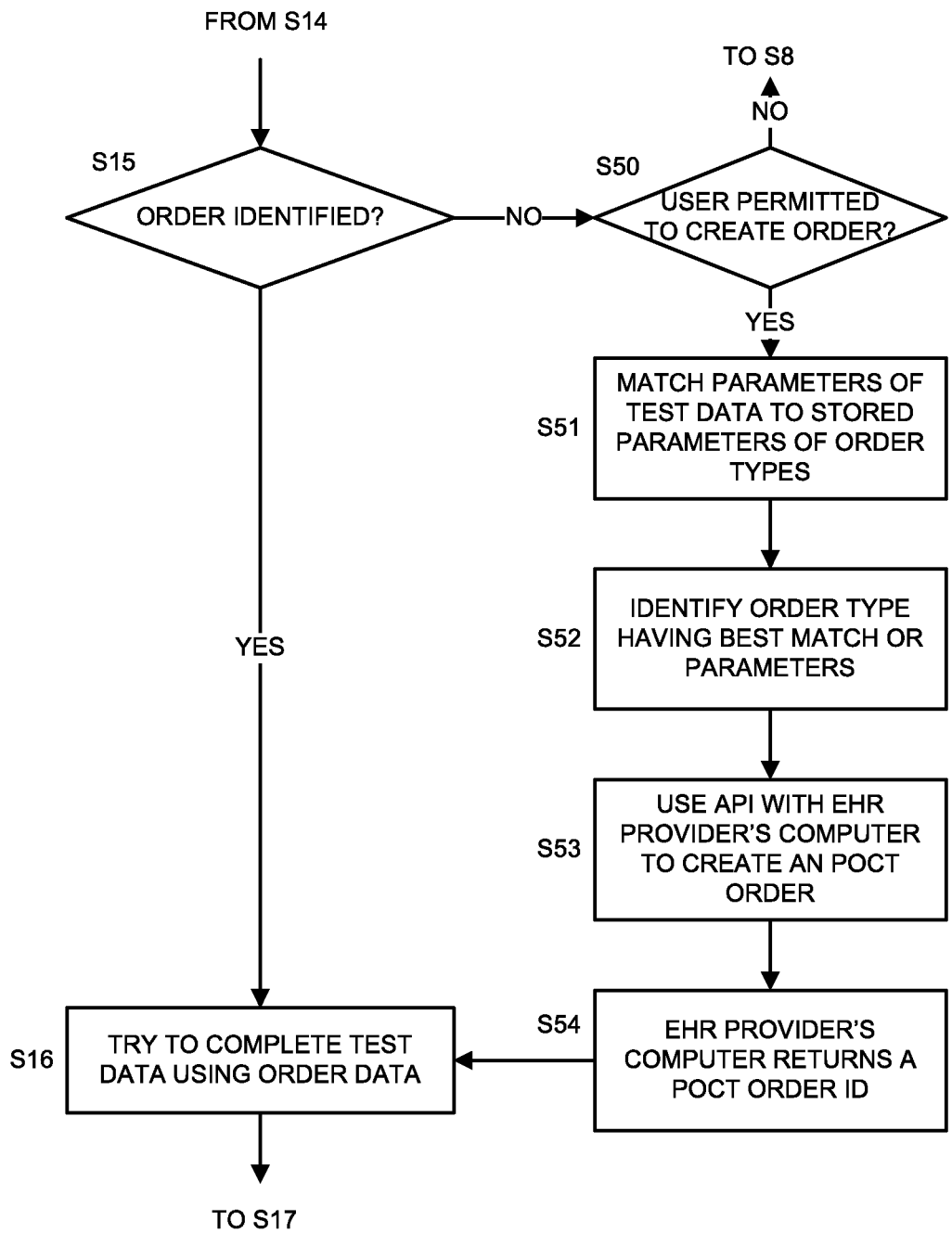
FIG. 6 is a flow diagram illustrating a method of allowing a user to create an EHR order according to one embodiment of the invention.

FIG. 6 illustrates an alternative embodiment in which an order number for a point of care test is automatically determined and used for the uploading of the point of care test data to the electronic health record provider's computer. The process can be implemented as an alternative to the manual processing required after step S15 in the flow diagram of FIG. 5.

If the order cannot be identified in step S15, in step S50, the process can determined whether the user is permitted to create an order for the point of care test in the electronic health record. If not, the process returns to step S8 as described with reference to FIG. 5. If the user is permitted to create an order, in step S51 parameters of the point of care test data are compared with and matched to parameters of order types stored in the order database 68. The order types can comprise sets of parameters defining format for order types accepted by electronic health providers. The match can indicate that the order type is suitable to be raised against the patient and for the test data to be used to fulfil it. In step S52 an order type having the best match to the parameters is identified and in step S53 the API to the electronic health provider's computer is used to create a point of care test order in the electronic health record for the patient. The electronic health record provider's computer then returns a point of care test order identifier to the service provider's computer 60 via the API in step S54. Also, point of care order data can be returned to the service provider's computer to assist with the completion of the point of care test data. Alternatively, it may be necessary for the service provider's computer 60 to make a request for the order identifier before the order identifier is returned.

The process can then return to step S16 of FIG. 5 for the process to try to complete the point of care test data using the point of care order data as described herein above with reference to FIG. 5.

Thus, this embodiment provides a method to reduce the reliance on the manual input of an order number or the inability to identify and retrieve an order by an automated process for the determination and creation of a point of care test order. Also, a user need not have to access an electronic health record provider's computer to of contact an electronic health provider to create a point of care test order before a point of care test result can be uploaded to the electronic health record for a patient.

Figure 7:
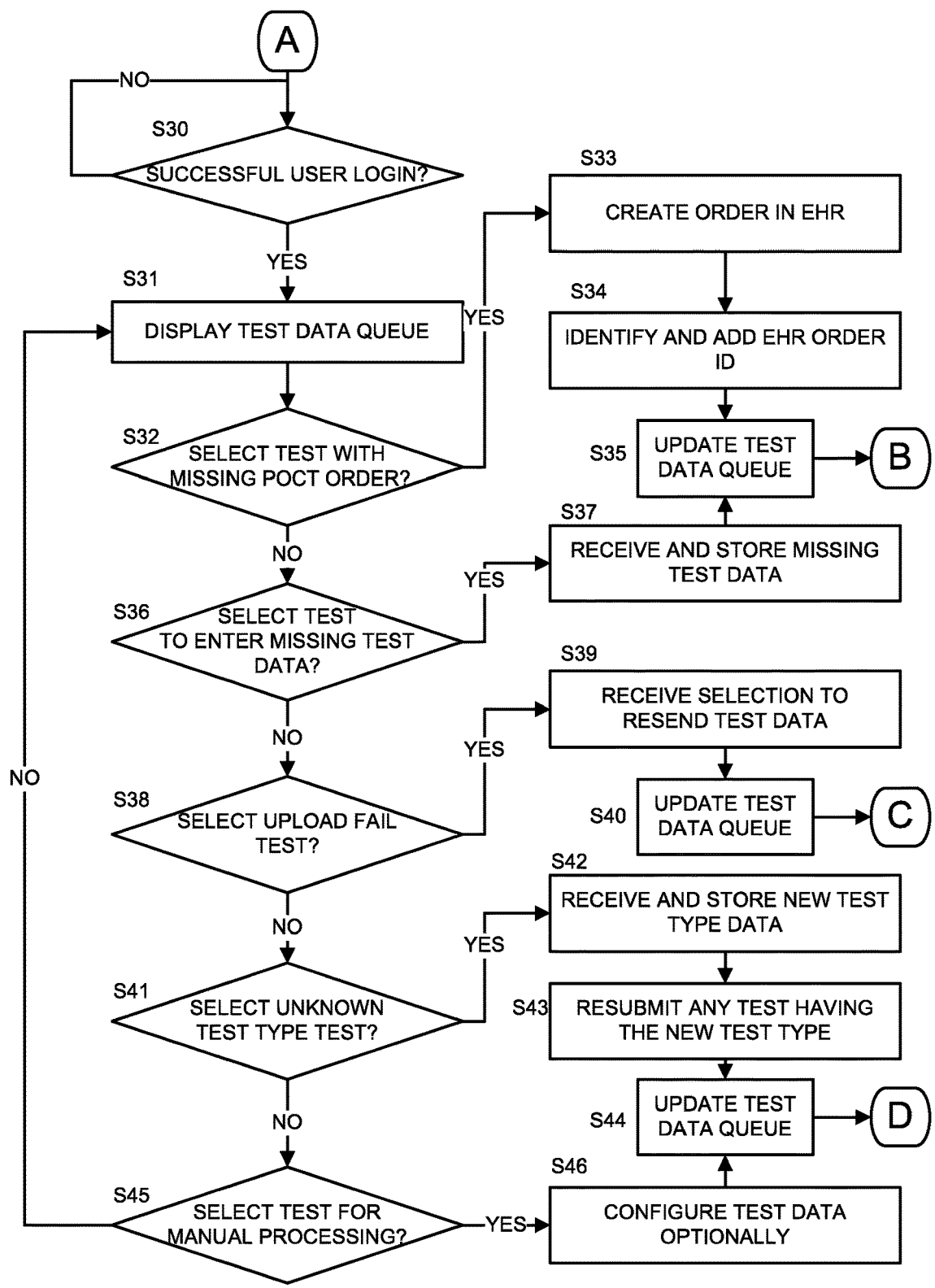
FIG. 7 is a flow diagram illustrating a method allowing a user to enter data and control the processing of the patient test data according to one embodiment of the invention

FIG. 7 is a flow diagram illustrating the process of the manual intervention on the point of care test data added to the queue for users.

An operator of a point of care device or any other authorised user can log into a web interface provided by the service provider's computer 60 in step S30. A queue of point of care tests are displayed for the used in step S31 to enable the user to select one. If in step S32 the user selects a test with a missing point of care test order, a user can request the creation of a point of care test order in an electronic health record for a patient in step S33. This may require the user to access the electronic health record provider's computer to contact the electronic health record provider or the service provider's computer may provide access to the electronic health record provider's computer using the API. Once the point of care test order is created in the patient's electronic health record it is assigned an order identifier and this can be identified by searching for unfulfilled orders for the patient and it can be added as part of the point of care test data in step S34. The test data in the queue can then be updated to remove the test in step S35 and the process returns to step S17 in FIG. 5.

If the user selects a test missing test data in step S36, the user can enter missing test parameters to complete the test data in step S37. The test data in the queue can then be updated to remove the test in step S35 and the process returns to step S17 in FIG. 5.

If the user selects a test that failed to upload in step S38, the user can select to resend the test data in step S39. The test data in the queue can then be updated to remove the test in step S40 and the process returns to step S18 in FIG. 5.

If the user selects a test of unknown test type in step S41, in step S42 the user can input data for a new test type for storage. The test and any other test having this test type can then be resubmitted for processing in step S43. The test data in the queue can then be updated to remove the test in step S44 and the process returns to step S9 in FIG. 5.

If the user selects a test in step S45 that has been marked for manual processing, the user can configure the test data manually in step S46. The test data in the queue can then be updated to remove the test in step S44 and the process returns to step S9 in FIG. 5. If the user does not select a test in step S45 that has been marked for manual processing, the process returns to step S31.

The form of the data structures used in embodiments will now be described. The data structures used in the processing system of the embodiments comprise:

POCT Test
   POC Facility ID
   Device Test Type ID
   Results ID
POCT Order (POCT Order ID)
   POCT order type
   Physician ID—the physician that ordered the test
   EHR record ID—for patient (the record will include the patient ID) Patient identifying information (possible additional information—not just reliant on EHR record data)
   Date
   Appointment information
   Facility ID
   EHR Order Type Code
POC Facility (POC Facility ID)
   POC computer IDs
   Operator IDs
   EHR ID and login details
   Physician ID—a physician can have a relationship with a facility
POC Computer (POC Computer ID)
   POC device IDs
Order Type Mapping
   EHR Order Type Code
   Device Test Type ID
   Analyte Mapping IDs
Analyte Mapping
   Analyte Mapping ID
   EHR Analyte Code
   Analyte ID
Device Test Type
   Device Test Type ID
   Device Test Type Name
   Device Type ID
   Analyte IDs
Analyte
   Analyte ID
   Analyte Name
Operator (Operator ID)
   Name
   Login details
Device Type
   Device Type ID
   Device instances
      Supported device test types
      Serial number
      Connection information including connection type, port no etc
Quality Control Data
   POC computer ID
   Operator ID
   Facility ID
   Time and date
   Result IDs
   Device ID
   Device type
   Test type
   Additional data e.g. comments
   Accept or reject by operator (reason input by operator)

Consumable type
Test Data
 POC computer ID
 Operator ID
 Facility ID
 Time and date
 Result ID
 Device ID
 Device type
 Test type
 Patient ID
 POCT Order ID (optional)
 Additional data e.g. comments
 Accept or reject my operator (reason input by operator)
 Consumable type
Result (Result ID)
 Analyte ID
 Value
 Units
 Abnormal
 Pass/Fail (quality control)

Point of care test data will comprise some common fields such as patient identifier, data and time of test, test type, and device identifier and some fields that are test specific e.g. for a urinalysis test the data can include data for glucose level and pH. Additional required data can be input by an operator, such as for a urinalysis test can include colour and clarity of the sample. The user interface for such a selection can provide a limited selection of color and clarity values that the operator has to choose from.

Continuing with the example of a urinalysis, an instantiation of the test type for a specific device would include a Device ID e.g. the serial number and data comprising: pH, glucose concentration, colour, clarity, ketone, blood, nitrite, protein, leukocyte esterase, bilirubin and specific gravity.

It can be seen from the data structure described above that parameters missing in the point of care test data such as the order identifier, and even the MRN for a patient can be determined by accessing the electronic health record for a patient. So long as the patient can be identified, such as by their full name and date of birth, their electronic health record can be identified and the data contained therein used to assist in the completion of the point of care test data for upload to the electronic medical record. If the point of care test includes an order identifier, the data stored for the order can be used to assist in the completion of the test data. If there is no order, the service provider's computer can deduce an order type and request the creation of that type of order in the electronic medical record for the patient, so that the order identifier can be included in the test data and the test data can be uploaded to the electronic health record. Alternatively the POCT data can be submitted to the EHR directly against the patient, if it is permitted by the EHR to upload POCT data without an order.

In one embodiment, the electronic health record provider's computer includes a workflows system that generates notifications and/or verification requests when point of care test data is uploaded into the electronic medical records. Some electronic health record providers set their workflow to send out notifications of a test data upload and may send a request for verification of an uploaded test data based on the setting of flags or parameters in the electronic health record computer. In order to avoid unwanted notifications and/or verification requests being sent out, the API between the service provider's computer and the electronic health record provider's computer enables the service provider's computer to set the flags or parameters in the electronic health record provider's computer for the notifications and/or verifications in accordance with parameters stored by the service provider's computer, such as in the point of care test data. For example, when uploading test data, the service provider's computer can set the flags or parameters for the test data according to the site of the point of care test, the facility used, the location, the point of care device, the operators, or the test type.

This embodiment enables the health care provider administrators to provide their notification and/or verification requirement to the service provider's computer for storage and use in the control of the flags when uploading point of care test data to electronic health record provider's computers.

In the described embodiments of the invention, the provision of the data warehouse 600 enables centralized and common detailed reports on patient tests for multiple EHR providers, POC devices, operators, POC facilities, test types, regulatory compliance, and even POC consumable user for POC devices from the same manufacturer or supplier.

Although in the embodiments described above the POC data is collected from POC devices by a POC computer, alternative embodiments include received test data directly from POC devices if the POC devices are capable of directly sending the test data to the server.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

The invention claimed is:

1. A server system for processing patient test data from at least one point of care device, the server system comprising:
 a test data interface for receiving point of care test data for a patient from at least one point of care device over a communication network;
 an electronic health record provider interface for interfacing with a plurality of electronic health record provider computers over the communication network, wherein the electronic health record provider interface includes a plurality of electronic health record modules, each electronic health record module having an application programming interface (API) specific to one of the plurality of electronic health record provider computers, the plurality of electronic health record provider computers storing electronic health records for patients;
 program memory storing computer code; and
 a processor for reading and implementing the computer code in the program memory;
 wherein the program memory stores computer code for implementation by the processor to;
  control the test data interface to receive the point of care test data for the patient from at least one point of care device, wherein the point of care test data is received as a signal in a format specific to a point of care device from which the point of care test data has been received,
  control the test data interface to detect an identity of the point of care device by analysing the received point of care test data,
  control the test data interface to execute a device specific module identified dependent on the detected identity of the point of care device on the point of care test data to determine a test type by accessing a stored library of test type objects, and to reformat the received point of care test data according to the determined test type to generate reformatted point of care test data in a common format for electronic health record providers, identify an electronic health record module of the plurality of electronic health record modules based on the reformatted point of care test data, wherein an API for the electronic health record module is determined that allows the server system to transmit the point of care test data to a corresponding electronic health record provider computer of the plurality of electronic health record provider computers;

process the reformatted point of care test data to identify additional required data missing from the point of care test data for the patient according to electronic health record provider requirements for the point of care test data, control the electronic health record provider interface to retrieve electronic health record data for the patient from said electronic health record provider computer in response to the identified additional required data missing from the point of care test data for the patient according to electronic health record provider requirements for the point of care test data, process the retrieved electronic health record data for the patient to automatically determine and add the identified additional required data to the reformatted point of care test data for the patient to form complete reformatted point of care test data for the patient without requiring an operator to input the required data missing from the point of care test data for the patient; and transmit the complete reformatted point of care test data for the patient using the API of the identified electronic health record module to the electronic health record provider computer over the communications network for inclusion in the electronic health record for the patient.

2. The server system according to claim 1, wherein the additional required data comprises an order identifier entered in the electronic health record for the patient indicating that the point of care test for the patient was ordered by a physician, and the retrieved electronic health record data comprises an order identifier from the electronic health record data for the patient.

3. The server system according to claim 2, wherein the additional required data includes additional data and the retrieved electronic health record data comprises an order identifier and associated order data from the electronic health record data for the patient.

4. The server system according to claim 1, wherein the computer code is adapted to be implemented by the processor to control the electronic health record provider interface to obtain the electronic health record provider requirements.

5. The server system according to claim 1, wherein the computer code is adapted to be implemented by the processor to store point of care test data that could not be automatically completed and to generate a notification to a user to enable the user to enter data to form complete point of care test data for the patient.

6. A method at a server system for processing patient test data from at least one point of care device, the method comprising:

receiving point of care test data for a patient from at least one point of care device over a communication network, wherein the point of care test data is received as a signal in a format specific to a point of care device from which the point of care test data has been received;

detecting an identity of the point of care device by analysing the received point of care test data, interfacing with a plurality of electronic health record provider computers over the communication network using an electronic health record provider interface, wherein the electronic health record provider interface includes a plurality of electronic health record modules, each electronic health record module having an application programming interface (API) specific to one of the plurality of health record provider computers, the plurality of electronic health record provider computers storing electronic health records for patients;

executing a device specific module identified dependent on the detected identity of the point of care device on the point of care test data to determine a test type by accessing a stored library of test type objects, and to reformat the received point of care test data according to the determined test type to generate reformatted point of care test data in a common format for electronic health record providers, identifying an electronic health record module of the plurality of electronic health record modules based on the reformatted point of care test data, wherein an API for the electronic health record module is determined that allows the server system to transmit the point of care test data to a corresponding electronic health record provider computer of the plurality of electronic health record provider computers;

processing the reformatted point of care test data to identify additional required data missing from the point of care test data for the patient according to electronic health record provider requirements;

retrieving electronic health record data for the patient from an electronic health record provider's computer over the communication network in response to the identified additional required data, the electronic health record provider's computer storing electronic health records for patients;

processing the retrieved electronic health record data for the patient to automatically determine and add the identified additional required data to the reformatted point of care test data for the patient to try to form complete reformatted point of care test data for the patient without requiring an operator to input the required data missing from the point of care test data for the patient; and transmitting the complete reformatted point of care test data for the patient using the API of the identified electronic health record module to the electronic health record provider computer over the communications network for inclusion in the electronic health record for the patient.

7. The method according to claim 6, wherein the additional required data comprises an order identifier entered in the electronic health record for the patient indicating that the point of care test for the patient was ordered by a physician, and the retrieved electronic health record data comprises an order identifier from the electronic health record data for the patient.

8. The method according to claim 7, wherein the additional required data includes additional data and the retrieved electronic health record data comprises an order identifier and associated order data from the electronic health record data for the patient.

9. The method according to claim 6, further including using an electronic health record interface to obtain the electronic health record provider requirements from the electronic health record provider computer.

10. The method according to claim 6, including storing point of care test data that could not be completed and generating a notification to a user to enable the user to enter data to form complete point of care test data for the patient.

11. A server system for processing patient test data from at least one point of care device, the server system comprising:
a point of care interface for receiving point of care test data for a patient from at least one point of care device over a communication network;
an electronic health record provider interface for interfacing with a plurality of electronic health record provider computers over the communication network, wherein the electronic health record provider interface includes a plurality of electronic health record modules, each electronic health record module having an application programming interface (API) specific to one of the plurality of electronic health record provider computers, the plurality of electronic health record provider computers storing electronic health records for patients;
an order type memory storing data on parameters for types of orders for point of care tests ordered by physicians as order types, wherein different electronic health providers can require different order types;
program memory storing computer code; and
a processor for reading and implementing the computer code in the program memory;
wherein the program memory stores computer code for implementation by the processor to:
control the point of care interface to receive the point of care test data for the patient, wherein the point of care test data is received as a signal in a format specific to a point of care device from which the point of care test data has been received;
detect an identity of the point of care device by analysing the received point of care test data,
execute a device specific module identified dependent on the detected identity of the point of care device on the point of care test data to determine a test type by accessing a stored library of test type objects, and to reformat the received point of care test data according to the determined test type to generate reformatted point of care test data in a common format for electronic health record providers,
identify an electronic health record module of the plurality of electronic health record modules based on the reformatted point of care test data, wherein an API for the electronic health record module is determined that allows the server system to transmit the point of care test data to a corresponding electronic health record provider computer of the plurality of electronic health record provider computers,
process the reformatted point of care test data to identify if the received point of care test data does not include an order identifier identifying an order in an electronic health record for the patient for the point of care test for the patient according to electronic health record provider requirements, and compare parameters of the reformatted point of care test data to parameters of the stored types of orders to identify an order type if an order identifier is not included in the received point of care test data;
control the electronic health record provider interface to automatically create and add a point of care test order to the reformatted point of care test data and the electronic health record for the patient at the electronic health record provider computer without requiring an operator to create and add the point of care test order; and
transmit the reformatted point of care test data for the patient using the API of the identified electronic health record module to the electronic health record provider computer over the communications network for inclusion in the electronic health record for the patient.

12. The server system according to claim 11, wherein the computer code is adapted to be implemented by the processor to:
control the electronic health record provider interface to create a point of care test order in the electronic health record data for the patient at the electronic health record provider computer and to receive an order identifier for the created point of care test order from the electronic health record provider computer, and
add the received order identifier to the point of care test data.

13. A method at a server system for processing patient test data from at least one point of care device, the method comprising:
storing data on parameters for types of orders for point of care tests ordered by physicians as order types, wherein different electronic health providers can require different order types;
receiving point of care test data for a patient from at least one point of care device over a communications network using a point of care interface, wherein the point of care test data is received as a signal in a format specific to a point of care device from which the point of care test data has been received;
detecting an identity of the point of care device by analysing the received point of care test data;
executing a device specific module identified dependent on the detected identity of the point of care device on the point of care test data to determine a test type by accessing a stored library of test type objects, and to reformat the received point of care test data according to the determined test type to generate reformatted point of care test data in a common format for electronic health record providers;
interfacing with a plurality of electronic health record provider computers over the communication network using an electronic health record provider interface, wherein the electronic health record provider interface includes a plurality of electronic health record modules, each electronic health record module having an application programming interface (API) specific to one of the plurality of health record provider computers, the plurality of electronic health record provider computers storing electronic health records for patients;
processing the reformatted point of care test data to identify if the received point of care test data does not include an order identifier identifying an order in an electronic health record for the patient for the point of care test for the patient according to electronic health record provider requirements, and comparing parameters of the reformatted point of care test data to parameters of the stored types of orders to identify an order type if the received point of care test data does not include an order identifier identifying an order, wherein different electronic health providers can require different order types;

identifying an electronic health record module of the plurality of electronic health record modules based on the reformatted point of care test data, wherein an API for the electronic health record module is determined that allows the server system to transmit the point of care test data to a corresponding electronic health record provider computer of the plurality of electronic health record provider computers;

controlling the electronic health record provider interface to automatically create and add a point of care test order to the point of care test data and an electronic health record for the patient at the electronic health record provider computer without requiring an operator to create and add the point of care test order, the electronic health record provider's computer storing electronic health records for patients; and transmit the reformatted point of care test data for the patient using the API of the identified electronic health record module to the electronic health record provider computer over the communications network for inclusion in the electronic health record for the patient.

14. The method according to claim 13, wherein the electronic health record provider interface is controlled to create a point of care test order in the electronic health record data for the patient at the electronic health record provider computer and to receive an order identifier for the created point of care test order from the electronic health record provider computer, and the received order identifier is added to the point of care test data.

15. A non-transient storage medium storing computer readable code for controlling a computer to process patient test data from at least one point of care device, by:

controlling a test data interface to receive point of care test data for a patient from at least one point of care device over a communications network, wherein the point of care test data is received as a signal in a format specific to a point of care device from which the point of care test data has been received, controlling the test data interface to detect an identity of the point of care device by analysing the received point of care test data, interfacing with a plurality of electronic health record provider computers over the communication network using an electronic health record provider interface, wherein the electronic health record provider interface includes a plurality of electronic health record modules, each electronic health record module having an application programming interface (API) specific to one of the plurality of health record provider computers, the plurality of electronic health record provider computers storing electronic health records for patients, executing a device specific module identified dependent on the detected identity of the point of care device on the point of care test data to determine a test type by accessing a stored library of test type objects, and to reformat the received point of care test data according to the determined test type to generate reformatted point of care test data in a common format for electronic health record providers, identifying an electronic health record module of the plurality of electronic health record modules based on the reformatted point of care test data, wherein an API for the electronic health record module is determined that allows the server system to transmit the point of care test data to a corresponding electronic health record provider computer of the plurality of electronic health record provider computers, processing the reformatted point of care test data to identify additional required data missing from the received point of care test data for the patient according to electronic health record provider requirements for the point of care test data;

controlling an electronic health record provider interface to retrieve electronic health record data for the patient from an electronic health record provider's computer over the communication network in response to the identified additional required data, the electronic health record provider's computer storing electronic health records for patients;

processing the retrieved electronic health record data for the patient to automatically determine and add the identified additional required data to the reformatted point of care test data for the patient to form complete reformatted point of care test data for the patient without requiring an operator to input the required data missing from the point of care test data for the patient; and transmit the complete reformatted point of care test data for the patient using the API of the identified electronic health record module to the electronic health record provider computer over the communications network for inclusion in the electronic health record for the patient.

16. A non-transient storage medium storing computer readable code for controlling a computer to process patient test data from at least one point of care device, by:

storing data on parameters for types of orders for point of care tests ordered by physicians as order types, wherein different electronic health providers can require different order types;

controlling a point of care interface to receive point of care test data for a patient from at least one point of care device over a communications network, wherein the point of care test data is received as a signal in a format specific to a point of care device from which the point of care test data has been received, controlling the test data interface to detect an identity of the point of care device by analysing the received point of care test data, interfacing with a plurality of electronic health record provider computers over the communication network using an electronic health record provider interface, wherein the electronic health record provider interface includes a plurality of electronic health record modules, each electronic health record module having an application programming interface (API) specific to one of the plurality of health record provider computers, the plurality of electronic health record provider computers storing electronic health records for patients, executing a device specific module identified dependent on the detected identity of the point of care device on the point of care test data to determine a test type by accessing a stored library of test type objects, and to reformat the received point of care test data according to the determined test type to generate reformatted point of care test data in a common format for electronic health record providers, identifying an electronic health record module of the plurality of electronic health record modules based on the reformatted point of care test data, wherein an API for the electronic health record module is determined that allows the server system to transmit the point of care test data to a corresponding electronic health record provider computer of the plurality of electronic health record provider computers, processing the reformatted point of care test data to identify if the point of care test data does not include an order identifier identifying an order in an electronic health record for the patient for the point of care test for the patient according to electronic health record provider requirements, and comparing parameters of the reformatted point of care test data to parameters of stored types of orders to identify an order type if the received point of care test data does not include an order identifier identifying an order, wherein different electronic health providers can require different order types; and controlling an electronic health record provider's interface to automatically create and add a point of care test order to the reformatted point of care test data and an electronic health record for the patient at an electronic health record provider's computer without requiring an operator to create and add the point of care test order, the electronic health record provider's computer storing electronic health records for patients; and transmitting the reformatted point of care test data for the patient using the API of the identified electronic health record module to the electronic health record providers computer over the communications network for inclusion in the electronic health record for the patient.

\* \* \* \* \*